(12) United States Patent
Rezach

(10) Patent No.: US 9,017,386 B2
(45) Date of Patent: Apr. 28, 2015

(54) ILIAC CONNECTORS

(71) Applicant: Warsaw Orthopedic, Inc., Warsaw, IN (US)

(72) Inventor: William Alan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/791,315

(22) Filed: Mar. 8, 2013

(65) Prior Publication Data

US 2014/0257399 A1    Sep. 11, 2014

(51) Int. Cl.
*A61B 17/88* (2006.01)
*A61B 17/70* (2006.01)

(52) U.S. Cl.
CPC ......... *A61B 17/7037* (2013.01); *A61B 17/7038* (2013.01); *A61B 17/7041* (2013.01); *A61B 17/7055* (2013.01)

(58) Field of Classification Search
USPC .............. 606/250–278, 53–59; 403/385, 396, 403/398, 400
See application file for complete search history.

(56) References Cited

U.S. PATENT DOCUMENTS

| | | | |
|---|---|---|---|
| 5,643,263 A | 7/1997 | Simonson | |
| 5,645,544 A | 7/1997 | Tai et al. | |
| 6,551,318 B1 * | 4/2003 | Stahurski | 606/252 |
| 6,673,073 B1 * | 1/2004 | Schafer | 606/278 |
| 6,872,209 B2 | 3/2005 | Morrison | |
| 7,867,255 B2 | 1/2011 | Miller et al. | |
| 8,097,023 B2 | 1/2012 | Cline, Jr. et al. | |
| 8,246,658 B2 | 8/2012 | Rezach | |
| 8,317,834 B2 | 11/2012 | Rezach et al. | |
| 8,317,837 B2 | 11/2012 | Rezach et al. | |
| 8,668,721 B2 * | 3/2014 | Miller | 606/264 |
| 2008/0021456 A1 | 1/2008 | Gupta et al. | |
| 2010/0049253 A1 * | 2/2010 | Miller | 606/264 |
| 2011/0184416 A1 | 7/2011 | Rezach et al. | |
| 2012/0029571 A1 | 2/2012 | Schwab et al. | |
| 2012/0065691 A1 | 3/2012 | Simonson | |
| 2012/0179205 A1 | 7/2012 | Miller | |
| 2012/0253398 A1 | 10/2012 | Metcalf et al. | |

* cited by examiner

*Primary Examiner* — Mary Hoffman
*Assistant Examiner* — Tara R Carter

(57) ABSTRACT

A connector assembly comprising a connector, spinal rod receiver, a washer and a compression member is provided. The connector extends between a first end and a second end configured for coupling to a bone fastener. The first end of the connector contains an upper surface and a lower splined surface configured for mating with a lower splined surface of a washer disposed between the first end of the connector and the rod receiver. The rod receiver containing a receiver body coupled to a threaded shaft. The rod receiver is configured for receiving a spinal rod and is attachable to the first end of the connector for selectively adjusting the direction of at least a portion of a spinal rod. The compression member connects the receiver with the first end of the connector for securing the spinal rod into the receiver body. Methods of use are also disclosed.

17 Claims, 4 Drawing Sheets

ILIAC CONNECTORS

TECHNICAL FIELD

The present disclosure generally relates to medical devices for the treatment of musculoskeletal disorders, and more particularly to a spinal assembly and method that employs a connector and provides stabilization of vertebrae, which may include the sacroiliac region.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column. In another example, disorders of the sacroiliac joint can cause low back and radiating buttock and leg pain in patients.

Various pathologies of the human spine may be treated by stabilizing and properly positioning the vertebrae and joints of the spine. Some spinal implant assemblies rely on one or more rods as structural support for stabilizing and properly positioning components of the spine. Vertebral anchors such as bolts, screws, and hooks are typically secured to the vertebrae for connection to the one or more rods. These vertebral anchors must be positioned at various angles relative to the one or more rods to accommodate the anatomical structure of a patient, the physiological problem being treated, and the preference of the physician. It is difficult to provide secure connections between spinal support rods and vertebral anchors at the various angles that may be required, especially where there are different distances between rods and bolts and where components are located at different relative heights within the patient.

Spinal implants can be engaged to or along one or more vertebrae of the spinal column for the treatment of various spinal conditions or abnormalities. Elongate rods are commonly used to stabilize and support portions of the spinal column for treatment, either by fixing the spinal column or by permitting at least some degree of relative motion between the stabilized motion segments. Bone fasteners such as, for example, vertebral screws are provided to secure the elongate rods to one or more vertebrae at a particular location along the spinal column. In some instances, connectors or other types of coupling devices are used to interconnect the rods with the bone fasteners. Current connectors and coupling devices typically have a large footprint or outer profile, including numerous pieces that are not particularly easy to use or assemble, and/or are not sufficiently adjustable to accommodate for variations in the position and/or angular orientation of the bone fasteners (e.g., vertebral screws) relative to the elongate rods.

In some spinal implant assemblies, each bone fastener (e.g., vertebral screw) can be coupled to the rod with a connector. The connector attaches to a portion of a bone fastener and attaches to the rod.

Surgical treatment of spinal disorders includes fusion, fixation, discectomy, laminectomy and implantable prosthetics. During surgical treatment, one or more rods may be attached via fasteners to the exterior of two or more vertebral members. Fasteners may also be attached to iliac bone. Iliac connectors, also called lateral connectors, are used to connect iliac screws to a spinal rod. Seating the rod into these connectors can be difficult because, among other things, the angle between the rod and the connector is typically not 90 degrees, which requires that the rod be bent by the surgeon to conform it to the particular angle needed for treatment of the spinal disorder.

It would therefore be desirable to provide a spinal implant assembly having a connector configured to lock into the appropriate position at different angles in the coronal plane of the spine. Thus, there is a need for a spinal connector assembly that provides advantages over existing connector or coupling devices.

SUMMARY

A spinal connector assembly is provided having a rod receiver, where the components of the connector assembly are positioned above the rod receiver, which allows the connector to be rotatable about the rod. The spinal connector assembly provided allows the rod to be seated in the rod receiver at the appropriate angle without the need for bending the rod. In some embodiments, the spinal connector assembly provided has its components (e.g., washer, compression member, etc.) above the rod receiver so that the spinal connector has a low profile below the rod, which allows the connector to be moved in the desired angle and avoids the need for the surgeon to bend the rod.

Accordingly, a connector assembly for interconnecting a bone fastener and a spinal rod is provided. In one embodiment, there is a connector assembly for interconnecting a bone fastener and a spinal rod, the connector assembly comprising: a connector extending generally along a first rotational axis, having a first end and a second end disposed in co-axial orientation to one another, the first end defining a first cavity around an assembly axis and the second end of the connector configured to be coupled to a bone fastener; a spinal rod receiver having a receiver body configured to be disposed beneath the connector and having a second cavity disposed around the assembly axis, the second cavity configured for receiving a spinal rod, the spinal rod receiver configured to substantially circumscribe the spinal rod and contact the first cavity of the connector for selectively adjusting the direction of at least a portion of the rod and/or connector in a coronal plane; and a compression member for securing at least a portion of the rod in the receiver body, the compression member configured to be disposed above the connector and contact the first cavity of the connector and the spinal rod receiver.

In one particular embodiment, in accordance with the principles of the present disclosure, the connector assembly comprises a connector, a spinal rod receiver, a washer and a compression member. In various embodiments, the connector extends generally along a first rotational axis, having a first end and a second end disposed in co-axial orientation to one another, the first end defining a first cavity around an assembly axis and the second end of the connector adapted to be coupled to a bone fastener. The spinal rod receiver has a receiver body coupled to a threaded shaft defining a second threaded cavity and in co-axial orientation with the receiver body. The receiver body defines a third cavity around the assembly axis, the third cavity for receiving an implant, for example, a spinal rod. In some embodiments, the rod receiver substantially circumscribes the spinal rod and is further attachable to the first end of the connector for selectively adjusting the direction of at least a portion of the rod in a coronal plane. The washer has an upper face and a lower face, the washer defines a fourth cavity around the assembly axis substantially circumscribing the assembly axis. The washer is slidingly coupled to the receiver body, the upper face of the washer being splined or ridged and rotatable 360 degrees in predetermined angular increments in place relative to the first end of the connector to adjust and/or fix the direction of at least a portion of the rod in the coronal plane. The compression member has a hexagonal nut coupled to a retaining flange which has two opposite ends and defines a fifth cavity around the assembly axis, the hexagonal nut being co-axial with and engaging with the first end of the connector and the spinal rod receiver, extending through the first cavity of the first end of the connector to engage with the second threaded cavity of the threaded shaft of the rod receiver for securing at least a portion of the rod in the receiver body.

In some embodiments, the spinal rod receiver comprises a receiver body coupled to an internally threaded collar in co-axial orientation with the receiver body. The receiver body defines a second cavity around the assembly axis, the second cavity for receiving a spinal rod. The internally threaded collar defines a third cavity. The rod receiver substantially circumscribes the spinal rod and is further attachable to the first end of the connector for selectively adjusting the direction of at least a portion of the rod in a coronal plane. In other embodiments, the compression member comprises a hexagonal nut coupled to a retaining flange, the retaining flange having two opposite ends, one end defining a fifth cavity around the assembly axis for receiving the hexagonal nut, the other end of the retaining flange coupled to a threaded shaft, the threaded shaft extending through the fourth cavity of the washer into the threaded collar of the receiver body to secure at least a portion of the rod into the receiver body.

In yet another embodiment, a method for treating a disorder is provided. The method comprises the steps of providing an implant assembly which comprises a bone fastener including a proximal portion and a distal portion, the proximal portion including a bore that defines a first axis, the distal portion defining a longitudinal axis disposed transverse to the first axis; a connector extending generally along a first rotational axis, having a first end and a second end disposed in co-axial orientation to one another, the first end defining a first cavity around an assembly axis and the second end of the connector adapted to be coupled to the bone fastener; a spinal rod receiver having a receiver body coupled to a threaded shaft defining a second threaded cavity and in co-axial orientation with the receiver body, the receiver body defining a third cavity around the assembly axis, the third cavity for receiving a spinal rod, the rod receiver substantially circumscribing the spinal rod and further attachable to the first end of the connector for selectively adjusting the direction of at least a portion of the rod in a coronal plane; a washer having an upper face and a lower face, the washer defining a fourth cavity around the assembly axis substantially circumscribing and slidingly coupled to the receiver body, the upper face of the washer being splined or ridged, the upper splined face rotatable 360 degrees in predetermined angular increments in place relative to the first end of the connector to adjust and/or fix the direction of at least a portion of the rod in the coronal plane; and a compression member having a hexagonal nut coupled to a retaining flange having two opposite ends and defining a fifth cavity around the assembly axis, the hexagonal nut co-axial with and engaging with the first end of the connector and the spinal rod receiver, extending through the first cavity of the first end of the connector to engage with the second threaded cavity of the threaded shaft of the rod receiver for securing at least a portion of the rod in the receiver body; attaching the distal portion of the bone fastener to an iliac bone; disposing an implant in the receiver body such that the implant is in co-axial relationship with the first end of the connector; selectively rotating the implant relative to the lower splined face of the first end of the connector to adjust and/or fix the direction of at least a portion of the implant in the coronal plane; and locking the rod receiver with the connector in a selected angular orientation of the implant relative to the connector.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which.

Figure 1:
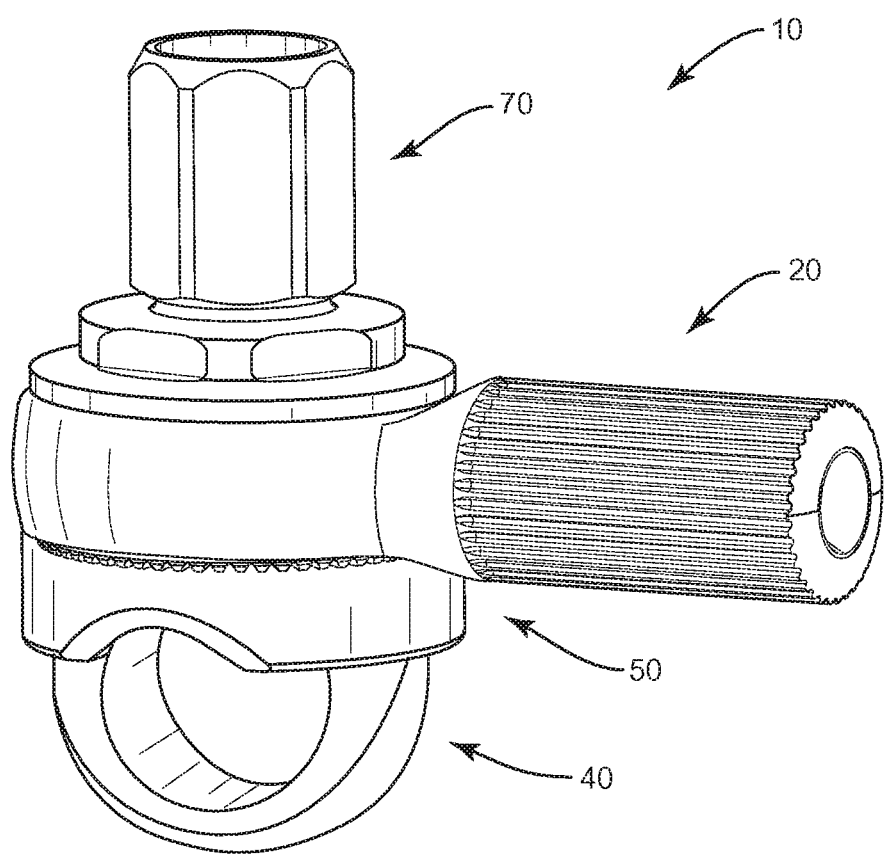
FIG. 1 is a perspective view of one particular embodiment of an implant assembly in accordance with the principles of the present disclosure.

Like reference numerals indicate similar parts throughout the figures. It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

The exemplary embodiments of the implant assembly and methods disclosed are discussed in terms of medical devices for the treatment of musculoskeletal disorders and more particularly, in terms of an implant assembly and method for treating a disorder. In one embodiment, the implant assembly includes a vertebral implant, such as, for example, a spinal rod and an iliac connector disposed with an iliac screw. It is envisioned that the implant assembly and methods disclosed may provide stability to a portion of the anatomy of a patient, such as, for example, vertebrae, a sacroiliac (SI) joint, iliac bone and maintain structural integrity while reducing stress on the SI joint and/or portions of the anatomy adjacent the SI joint.

The spinal connector assembly provided comprises a rod receiver, where the components of the connector assembly are positioned above the rod receiver, which allows the connector to be rotatable about the rod. The spinal connector assembly provided allows the rod to be seated in the rod receiver at the appropriate angle without the need for bending the rod. In some embodiments, the spinal connector assembly provided has its components (e.g., washer, compression member, etc.) above the rod receiver so that the spinal connector has a low profile below the rod, which allows the connector to be moved in the desired angle and avoids the need for the surgeon to bend the rod.

In one embodiment, the implant assembly includes a sacroiliac connector having a connecting element disposed above a spinal rod. This configuration disposes a substantial portion of the connector material above a spinal rod to minimize the height of the connector below the spinal rod and to allow for rotation about the spinal rod. In one embodiment, the implant assembly includes a connector that can lock at different angles in a coronal plane of a body of a patient. This configuration facilitates connection of a spinal rod to an iliac screw and avoids rod bending due to misalignment of the component parts.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed implant assembly and methods may be alternatively employed in a surgical treatment with a patient in a prone or supine position, and/or employs various surgical approaches to the spine, including anterior, posterior, posterior mid-line, lateral, postero-lateral, and/or antero-lateral approaches, and in other body regions. The present disclosure may also be alternatively employed with procedures for treating the lumbar, thoracic and pelvic regions of a spinal column. The implant assembly and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

As used herein, it is understood that the term "coronal plane" includes any plane of section in the anatomical position that generally passes vertically through the human body and is generally perpendicular to both the median (or sagittal) plane and the horizontal (or axial or transverse) plane, generally dividing the human body into anterior and posterior sections, and further includes any plane of section in the anatomical position that generally passes vertically through the human body, is generally perpendicular to the horizontal (or axial or transverse) plane, and is generally angularly oriented from the median (or sagittal) plane at an angle of orientation ranging from greater than zero degrees up to and including ninety degrees.

Furthermore, as used herein, it is understood that the term "sagittal plane" includes any plane of section in the anatomical position that generally passes vertically through the human body in the prone position and is generally perpendicular to both the coronal plane and the horizontal (or axial or transverse) plane, generally dividing the human body into left and right sections, and further includes any plane of section in the anatomical position that generally passes vertically through the human body in the prone position, is generally perpendicular to the horizontal (or axial or transverse) plane, and is generally angularly oriented from the coronal plane at an angle of orientation ranging from greater than zero degrees up to and including ninety degrees.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The following discussion includes a description of a surgical system including an implant assembly, related components and exemplary methods of employing the implant assembly in accordance with the principles of the present disclosure. Alternate embodiments are also disclosed. Reference will now be made in detail to the exemplary embodiments of the present disclosure, which are illustrated in the accompanying figures. Turning now to FIGS. 1 to 4, there are illustrated surgical implant assemblies and their components including an implant assembly in accordance with the principles of the present disclosure.

The components of the implant assembly can be fabricated from biologically acceptable materials suitable for medical applications, including metals, synthetic polymers, ceramics and bone material and/or their composites, depending on the particular application and/or preference of a medical practitioner. For example, the components of the implant assembly, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the implant assembly may have material composites, including the above materials, to achieve various desired characteristics such as strength, rigidity, elasticity, compliance, biomechanical performance, durability and radiolucency or imaging preference. The components of the implant assembly, individually or collectively, may also be fabricated from a heterogeneous material such as a combination of two or more of the above-described materials. The components of the implant assembly may be monolithically formed, integrally connected or include fastening elements and/or instruments, as described herein.

Figure 2:
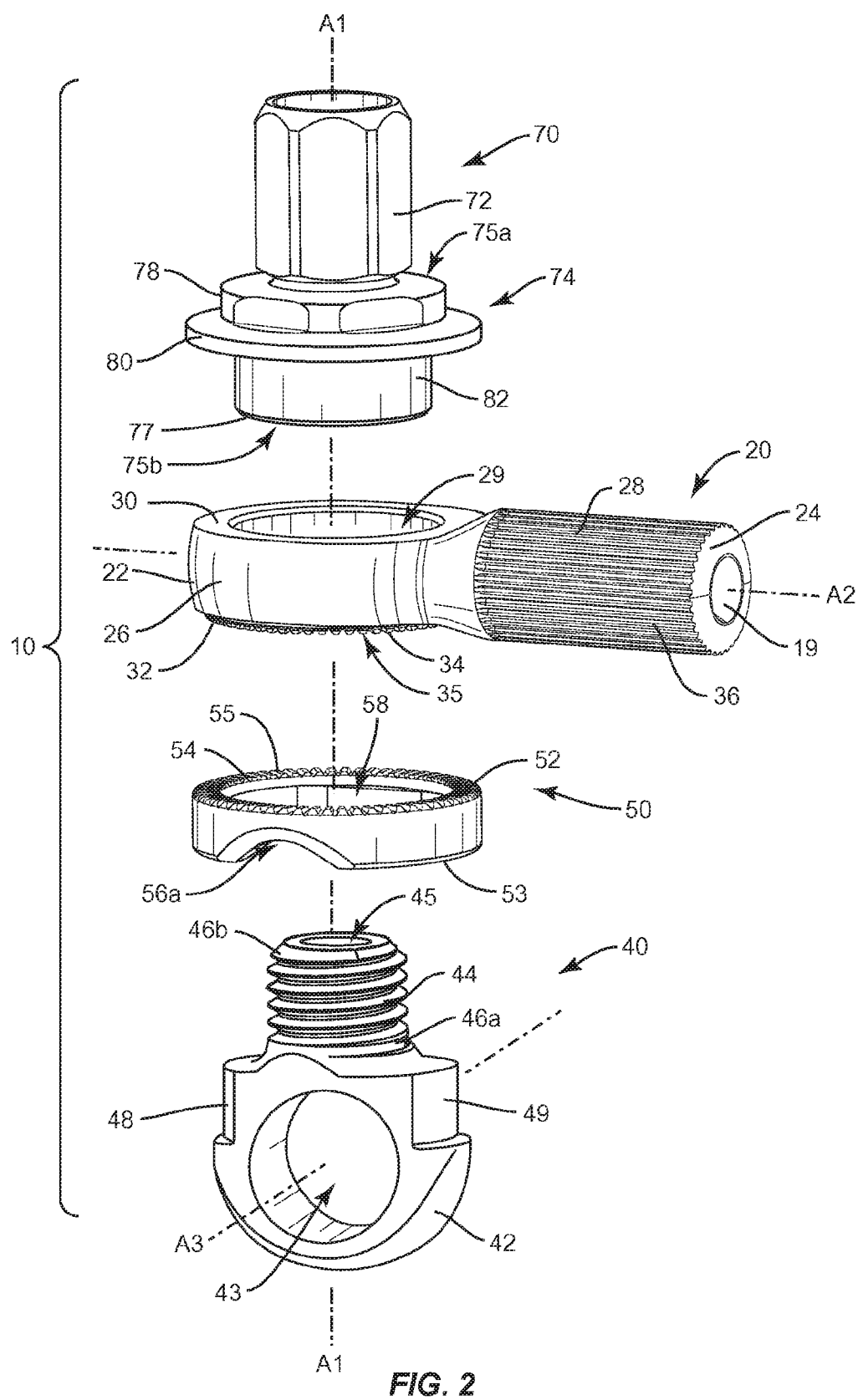
FIG. 2 is an exploded perspective view of components of the implant assembly shown in FIG. 1 with parts separated.

The connector assembly described herein is configured for attachment to vertebrae and/or iliac bone during surgical treatment of a spinal disorder, examples of which being discussed herein. With reference to FIG. 1 and FIG. 2, the connector assembly 10 includes a connector 20, a rod receiver 40, a washer 50 and a compression member 70. Connector assembly 10 extends generally along assembly axis A1 and is configured to interconnect a bone anchor member, for example, an iliac bone screw (not shown) with an elongate support member, for example, a spinal rod (shown in FIG. 4). Additionally, it should be understood that the connector assembly 10 may be used to interconnect various other types and configurations of spinal implants or devices, and is not limited to interconnecting a bone anchor member with an elongate support member. For example, the connector assembly 10 may alternatively be used to interconnect a pair of elongate support members, interconnect a bone anchor member with a stem associated with a coupling device, interconnect an elongate support member with a stem associated with a coupling device, or interconnect other types and configurations of spinal implants or devices. It should also be understood that the connector assembly 10 may be used in fields outside of the spinal field including, for example, in fixation or stabilization systems that are attached to other bony structures including the pelvis, the skull and/or the occiput, long bones, or other bony structures that would occur to those having ordinary skill in the art.

With reference to FIG. 2, connector 20 extends generally along a second rotational axis A2 between a first end 22 and a second end 24. First end 22 includes a disk 26 and an extension element 28. Disk 26 is disposed in a co-axial orientation with second end 24 of connector 20 around second rotational axis A2. Disk 26 is substantially circular and defines a first cavity 29 around assembly axis A1 which traverses first axis A2. It is envisioned that all or only a portion of disk 26 may have alternate cross section configurations, such as, for example, oval, oblong, triangular, square, polygonal, irregular, uniform, non-uniform, offset, staggered, undulating, arcuate, variable and/or tapered. Disk 26 has an upper surface 30 and lower surface 32. Lower surface 32 contains splines or ridges 34 defining first splined surface 35. First splined surface 35 is circumferentially disposed about first cavity 29. First splined surface 35 of disk 26 is configured to mate with splines on a surface of a washer as further described in more detail below to releasably fix spinal rod receiver 40 with connector 20 in a selected rotatable position in a coronal plane of the body relative to an iliac bone screw (not shown). In some embodiments splines 34 on lower surface 32 can be replaced with ridges, teeth or any other kind of grooves.

In one embodiment, disk 26 and extension element 28 are formed unitarily integral with one another to provide the connector 20 as a solid body core or a monolithic single-piece structure where disk 26 and the extension element 28 are non-movable relative to one another. However, other configurations of the connector 20 are also contemplated where disk 26 and extension element 28 are formed separately and coupled to one another by a connection mechanism, either in a rigid, non-movable embodiment or in an embodiment wherein disk 26 and extension element 28 are movably coupled to one another to allow relative translational movement therebetween generally along or transverse to the rotational axis A2 and/or relative rotational movement therebetween about assembly axis A1.

With reference to FIG. 2, second end 24 of connector 20 includes an extension element 28 having a generally cylindrical outer surface comprising axial splines 36 circumferentially disposed about the outer surface of extension element 28 of second end 24. Axial splines 36 are engageable with axial splines disposed about the inner surface of a cavity in the head of an iliac bone screw (not shown) for selective angular fixation of the bone screw with connector 20. Axial splines 36 include a plurality of individual spline members that extend in parallel relation about the outer surface of second end 24. The configuration of axial splines 36 provides at least a portion of a mounting and alignment configuration for aligning and mounting a bone screw with connector 20 and rod receiver 40 during a surgical treatment. In some embodiments, connector 20 comprises bore 19 that is configured to engage a fastener (e.g., bone screw) that, in some embodiments, can mate the fastener with the bone from the iliac region. In some embodiments, it is contemplated that bore 19 can comprise a friction fit, pressure fit, locking protrusion/recess, locking keyway and/or adhesive to secure the fastener.

It is envisioned that the outer surface of second end 24 may have alternate cross section configurations, such as, for example, oval, oblong, triangular, rectangular, square, polygonal, irregular, uniform, non-uniform, variable and/or tapered. It is further envisioned that all or only a portion of the outer surface of second end 24 may have alternate surface configurations, such as, for example, rough, threaded for connection with other instruments, arcuate, undulating, porous, semi-porous, dimpled, polished and/or textured according to the requirements of a particular application. It is further envisioned that the outer surface of second end 24 may have alternate cross section configurations, such as, for example, oval, oblong, triangular, rectangular, square, polygonal, irregular, uniform, non-uniform, variable and/or tapered.

With further reference to FIG. 2, second end 24 of connector 20 is configured for disposal within a cavity of the head of a bone screw along second axis A2 in the coronal plane of a patient's body. Second end 24 of connector 20 is moveable and configured to rotate about axis A2 relative to the head of a bone fastener, for example, an iliac bone screw. It is envisioned that second end 24 may be inserted into the head cavity of the bone fastener (not shown). Second end 24 is moved within the head cavity of the bone fastener in the coronal plane by sliding second end 24 relative to the head cavity of the bone fastener. The head cavity of the bone fastener is engageable with second end 24 to align the component parts in relative rotatable alignment in angular increments about their relative circumferential surfaces. The angular increments correspond to a spline teeth angle of splines 36. It is contemplated that the spline teeth angle may be in a range of approximately 5 to 20 degrees. In some embodiments, second end 24 of connector 20 can define an aperture 37 available for connecting connector 20 to other bone implants.

Figure 3:
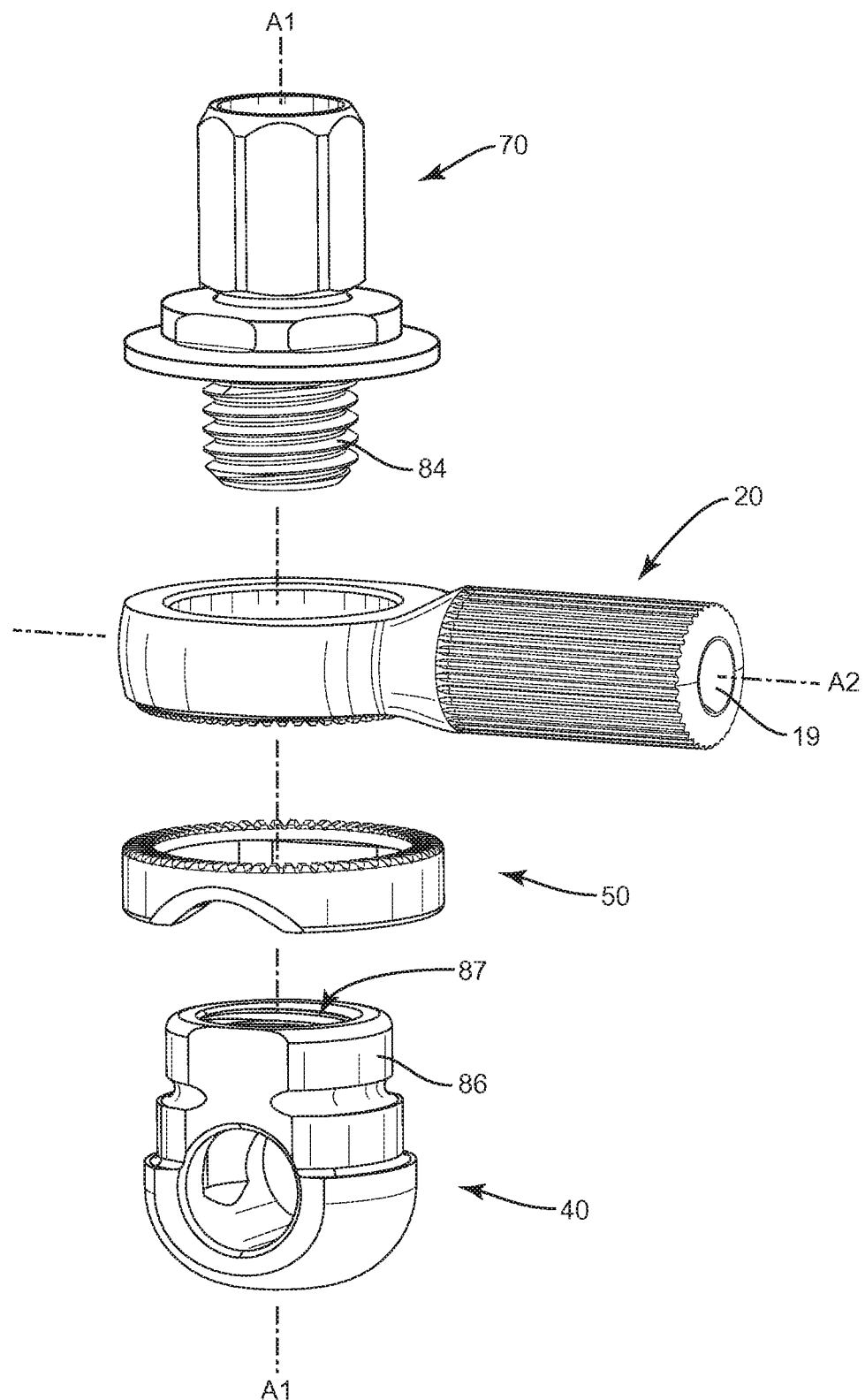
FIG. 3 is an exploded perspective view of components of another embodiment of an implant assembly in accordance with the principles of the present disclosure.
Figure 4:
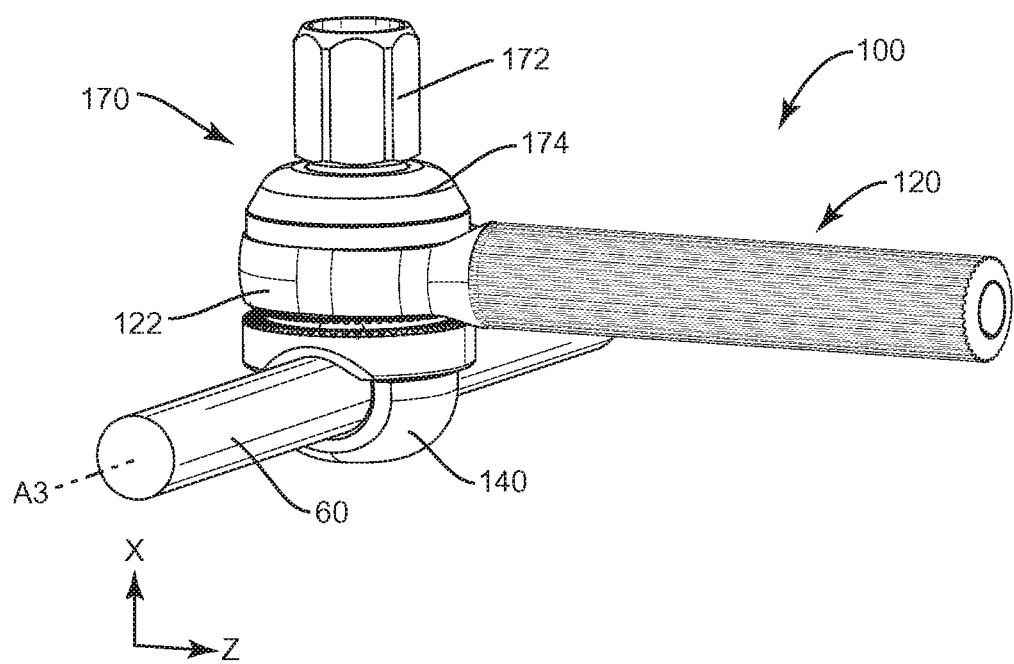
FIG. 4 is a perspective view of yet another embodiment of an implant assembly in accordance with the principles of the present disclosure.

With reference to FIGS. 2 to 4, connector assembly 10 further comprises a rod receiver 40 comprising a receiver body 42 defining an implant cavity 43 and an externally threaded shaft 44. Rod receiver 40 is attachable to first end 22 or disk 26 of connector 20 and is selectively rotatable in the coronal plane of the body and selectively fixable in a position within the coronal plane. Rod receiver 40 includes a receiver body 42 having a cylindrical ring shape defining an implant cavity 43 around assembly axis A1. It is envisioned that implant cavity 43 is configured to receive an implant member, for example a spinal rod 60 as shown in FIG. 4. Receiver body 42 may be a cylindrical band such that the interior surface of implant cavity 43 surrounds the entire exterior surface of spinal rod 60. It is also envisioned that receiver body 42 of rod receiver 40 may have alternate cross section configurations, such as, for example, oval, oblong, triangular, rectangular, square, polygonal, irregular, uniform, non-uniform, variable and/or tapered.

Implant cavity 43 is configured to receive and movably support at least a portion of an implant, such as, for example, a spinal rod 60, such that spinal rod 60 can rotate and/or slide axially within implant cavity 43 about third axis A3 such that a spinal rod disposed in implant cavity 43 is rotatable in the coronal plane of the patient's body, relative to first end 22 of connector 20 in a configuration for selective fixation with first end 22 of connector 20. It is contemplated that at least a portion of the implant may be disposed within implant cavity 43 for relative movement in orientations relative to first assembly axis A1.

In various embodiments, rod receiver 40 includes a first locking part, such as, for example, a threaded shaft 44 extending from rod receiver body 42 around assembly axis A1 and configured to engage a second locking part, such as, for example, a hexagonal nut 72 to secure rod receiver 40 with connector 20. Threaded shaft 44 is co-axial with rod receiver body 42 about assembly axis A1. Threaded shaft 44 extends generally along assembly axis A1 between a first end 46a and a second end 46b opposite each other. First end 46a is coupled to and co-axial with rod receiver body 42. In some embodiments, at opposite end 46b, threaded shaft 44 defines a second cavity 45 around assembly axis A1 for coupling with hexagonal nut 72.

In various embodiments, the connector assembly 10 is configured to be rotated around the rod about axis A3 before it is tightened using hexagonal nut 72. The connector 20 of the connector assembly 10 is configured to be rotated about assembly axis A1. In this way, the surgeon can rotate the rod receiver and/or the connector so that the desired angle to fasten the connector assembly to the bone can be achieved.

In certain embodiments, it is contemplated that threaded shaft 44 may be disposed in other orientations relative to receiver body 42, such as, for example, other angular orientations such as acute or obtuse, co-axial and/or may be offset or staggered. In one embodiment, as illustrated in FIG. 2, shaft 44 can be shaped as a threaded male fastener for coupling receiver body 42 and washer 50 through the first end 22 of connector 20 to compression member 70.

In other embodiments, it is envisioned that rod receiver 40 may be coupled with connector 20 in alternate fixation configurations, such as, for example, friction fit, pressure fit, locking protrusion/recess, locking keyway and/or adhesive. It is further contemplated that all or only a portion of lower surface 32 of disk 26 may have alternate surface configurations to enhance fixation with the splined upper surface of washer 50, such as, for example, rough, arcuate, undulating, mesh, porous, semi-porous, dimpled and/or textured according to the requirements of a particular application.

With further reference to FIGS. 2 and 4, implant assembly 10 includes a generally cylindrical washer 50 comprising an upper face 52 and a lower face 53, both defining a fourth cavity 58 co-axial with assembly axis A1. Washer 50 is disposed between receiver body 42 and lower surface 32 of first end 22 of connector 20, wherein at least a portion of the spinal rod (not shown) engages washer 50 when the spinal rod is inserted into receiver body 42. For example, in some embodiments, as illustrated in FIG. 2, washer 50 also comprises a recess 56a shaped to receive a spinal rod so as to engage washer 50 with the receiver body 42 in order to tightly secure the spinal rod. It is envisioned that receiver body 42 further comprises indents 48, 49 on each side in order to facilitate a tight engagement of washer 50 with receiver body 42 and the spinal rod.

With further reference to FIG. 2 upper face 52 of washer 50 defines a second splined surface 54 defined by axial splines 55 that mate with the splines 34 of first splined surface 35 of disk 26 to releasably fix rod receiver 40 with connector 20 in a selected rotatable position in a plane, such as, for example, a coronal plane of the body relative to the shaft of an iliac bone screw. It is contemplated that all or only a portion of second splined surface 54 may have alternate surface configurations to enhance fixation with connector 20, such as, for example, rough, arcuate, undulating, mesh, porous, semi-porous, dimpled and/or textured according to the requirements of a particular application. Splines 55 and the splines 34 on first splined surface 35 of disk 26 are configured to mesh such that rod receiver 40 (including implant cavity 43) and washer 50 can rotate and lock at different angles relative to connector 20 such that a vertebral rod 60 (shown only in FIG. 4) disposed in implant cavity 43 and below first end 22 of connector 20 can be selectively rotatable in a coronal plane of a body relative to first end 22 of connector 20 in a configuration for selective angular fixation with first end 22 of connector 20. It is envisioned that implant cavity 43 (or an implant received within implant cavity 43) may be rotated through an angle of 0 to 360 degrees relative to connector 20. Upper face 52 of washer 50 is locked in position relative to disk 26 by forcing upper face 52 of washer 50 and lower surface 32 of disk 26 into engagement. In one embodiment, upper face 52 of washer 50 and lower surface 32 of disk 26 are resiliently biased towards one another for fixed engagement.

With further reference to FIG. 2, in various embodiments, implant assembly 10 further comprises a compression member 70 configured to receive threaded shaft 44 of rod receiver 40 in order to secure a spinal rod to connector 20. In some embodiments, with further reference to FIG. 2, compression member 70 comprises hexagonal nut 72 and a retaining flange 74 in co-axial orientation with each other.

Hexagonal nut 72 can be a set screw having a break-off head useful for minimizing the height of the implant assembly above the rod. Retaining flange 74 has two opposite ends 75a, 75b and defines a fifth cavity 77 around assembly axis A1. Retaining flange 74 further contains a hexagonal shaped retaining plate 78 having chamfered or beveled edges. Hexagonal plate 78 is connected to a rim 80, which in turn is connected to a cylindrical connecting piece 82, all co-axial with each other, and together defining a fifth cavity 77 internally threaded for receiving a hexagonal nut 72 at end 75a, where threaded shaft 44 is configured to fit within end 75b of the hexagonal nut 72. It is contemplated that end 75b can comprise a friction fit, pressure fit, locking protrusion/recess, locking keyway and/or adhesive to secure the rod receiver 40.

In some embodiments retaining flange 74 is a unitary piece wherein hexagonal plate 78, rim 80 and cylindrical connecting piece 82 are welded together. In other embodiments, hexagonal plate 78, rim 80 and cylindrical piece 82 are separate elements threadingly connected to each other. In other embodiments, retaining flange 74 is internally threaded to form a female cavity with a fifth cavity 77 configured to receive the male protrusion of threaded shaft 44.

In certain other embodiments as illustrated in FIG. 3, internally threaded connecting piece 82 can be replaced with a second externally threaded shaft 84. As further illustrated in FIGS. 2 and 3, first threaded shaft 44 of rod receiver 40 can be replaced with a collar 86 defining a sixth internally threaded cavity 87, both around and co-axial with assembly axis A1. In use, the male protrusion of second externally threaded shaft 84 can engage the corresponding female internally threaded cavity 87 of collar 86 to secure a vertebral rod in receiver body 42.

In other embodiments, as illustrated in FIG. 4, connector assembly 100 comprises compression member 170 that comprises a hexagonal nut 172, and retaining receptacle 174, a semispherical unitary receptacle defining a seventh internally threaded cavity 177 (not shown) engageable through first end 122 of connector 120 with threaded shaft 144 (not shown) of rod receiver 140. Other components of connector assembly 100 as illustrated in FIG. 4 are identical to the same components described with reference to FIGS. 1 to 3.

In assembly, operation and use, an implant system comprising a bone screw, and implant assembly 10 comprising connector 20, receiver 40, washer 50 and compression member 70 is employed with a surgical procedure for treatment of a spinal disorder affecting a section of a spine and/or ilium bones of a pelvis of a patient, as discussed herein. The implant system may also be employed with other surgical procedures.

The implant system is employed with a surgical procedure for treatment of a condition or injury of an affected section of the spine including vertebrae, which may include sacrum, and/or ilium. It is contemplated that the implant system including bone screw and implant assembly 10 including connector 20, receiver 40, washer 50 and compression member 70 is attached to vertebrae and/or ilium for a surgical arthrodesis procedure, such as fusion, and/or dynamic stabilization application of the affected section of the spine to facilitate healing and therapeutic treatment.

In use, to treat the affected section of the spine and/or ilium bones of a pelvis, a medical practitioner obtains access to a surgical site including vertebra and/or ilium in any appropriate manner, such as through incision and retraction of tissues. It is envisioned that the implant system including a bone screw, and implant assembly 10 including connector 20, receiver 40, washer 50 and compression member 70 may be used in any existing surgical method or technique including open surgery, mini-open surgery, minimally invasive surgery and percutaneous surgical implantation, whereby the vertebrae and/or ilium is accessed through a micro-incision, or sleeve that provides a protected passageway to the area. Once access to the surgical site is obtained, the particular surgical procedure is performed for treating the bone disorder. The implant assembly 10 including connector 20, receiver 40 and compression member 70 is then employed to augment the surgical treatment. The implant system including a bone screw, and implant assembly 10 including connector 20, receiver 40, washer 50 and compression member 70 can be delivered or implanted as a pre-assembled device or can be assembled in situ. The implant assembly may be completely or partially revised, removed or replaced.

In some embodiments, there is a method for treating a disorder, the method comprising providing an implant assembly comprising: a bone fastener including a proximal portion and a distal portion, the proximal portion including a bore that defines a first axis, the distal portion defining a longitudinal axis disposed transverse to the first axis, a connector extending generally along a first rotational axis, having a first end and a second end disposed in co-axial orientation to one another, the first end defining a first cavity around an assembly axis and the second end of the connector adapted to be coupled to the bone fastener; a spinal rod receiver having a receiver body coupled to a threaded shaft defining a second threaded cavity and in co-axial orientation with the receiver body, the receiver body defining a third cavity around the assembly axis, the third cavity for receiving a spinal rod, the rod receiver substantially circumscribing the spinal rod and further attachable to the first end of the connector for selectively adjusting the direction of at least a portion of the rod in a coronal plane; a washer having an upper face and a lower face, the washer defining a fourth cavity around the assembly axis substantially circumscribing and slidingly coupled to the receiver body, the upper face of the washer being splined or ridged, the upper splined face rotatable 360 degrees in predetermined angular increments in place relative to the first end of the connector to adjust and/or fix the direction of at least a portion of the rod in the coronal plane; and a compression member having a hexagonal nut coupled to a retaining flange having two opposite ends and defining a fifth cavity around the assembly axis, the hexagonal nut co-axial with and engaging with the first end of the connector and the spinal rod receiver, extending through the first cavity of the first end of the connector to engage with the second threaded cavity of the threaded shaft of the rod receiver for securing at least a portion of the rod in the receiver body; attaching the distal portion of the bone fastener to an iliac bone; disposing an implant in the receiver body such that the implant is in co-axial relationship with the first end of the connector; selectively rotating the implant relative to the lower splined face of the first end of the connector to adjust and/or fix the direction of at least a portion of the implant in the coronal plane; and locking the rod receiver with the connector in a selected angular orientation of the implant relative to the connector.

In one embodiment, the implant assembly includes an agent, which may be disposed, packed or layered within, on or about the components and/or surfaces of the implant assembly. It is envisioned that the agent may include bone growth promoting material, such as, for example, bone graft to enhance fixation of the fixation elements with vertebrae.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of the implant assembly can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It is envisioned that the use of microsurgical and image guided technologies may be employed to access, view and repair spinal deterioration or damage, with the aid of the implant assembly. Upon completion of a procedure employing the implant assembly described above, the surgical instruments and assemblies are removed and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A connector assembly for interconnecting a bone fastener and a spinal rod, the connector assembly comprising:
   a connector extending generally along a first rotational axis and having a first end and a second end disposed in co-axial orientation to one another, the first end defining a first cavity around an assembly axis and the second end of the connector comprising an extension element having a generally cylindrical outer surface comprising axial splines circumferentially disposed about the outer surface each extending parallel to the first rotational axis, wherein the first end of the connector includes a disk having an upper splined surface and a lower splined surface and defines the first cavity around the assembly axis for receiving a threaded shaft of the rod receiver;
   a spinal rod receiver having a receiver body configured to be disposed beneath the connector and having a second cavity disposed around the assembly axis, the second cavity configured for receiving a spinal rod, the spinal rod receiver configured to substantially circumscribe the spinal rod and contact the first cavity of the connector for selectively adjusting the direction of at least a portion of the rod and/or connector in a coronal plane;
   a compression member for securing at least a portion of the rod in the receiver body, the compression member configured to be disposed above the connector and contact the first cavity of the connector and the spinal rod receiver, wherein the spinal rod is rotatable to a selected angular orientation for fixation with the first end of the connector; and
   a washer having an upper splined surface configured to mate with the lower splined surface of the disk.

2. A connector assembly of claim 1, further comprising a washer having an upper face and a lower face, the washer defining a third cavity around the assembly axis and configured to substantially circumscribe and slidingly engage the receiver body, the upper face of the washer being splined or ridged and rotatable 360 degrees in predetermined angular increments relative to the first end of the connector to adjust and/or fix the direction of at least a portion of the rod in the coronal plane.

3. A connector assembly of claim 1, wherein the second end of the connector is adapted to extend through a bore defined in the bone fastener.

4. A connector assembly of claim 1, wherein the compression member comprises a hexagonal nut and a retaining flange in co-axial orientation with each other, the hexagonal nut having a break-off head, and the retaining flange internally threaded so as to threadingly receive the hexagonal nut at one end and a threaded shaft of the spinal rod receiver at the opposite end.

5. A connector assembly of claim 4, wherein the retaining flange further comprises a hexagonal plate, a rim and a cylindrical connecting piece, all internally threaded and serially coupled to each other.

6. A connector assembly of claim 1, wherein the compression member comprises a hexagonal nut coupled to an internally threaded semispherical receptacle having two opposite ends and defining an internally threaded cavity around the assembly axis, the hexagonal nut co-axial with the first end of the connector and the spinal rod receiver, extending through the first cavity of the first end of the connector to engage with the second cavity of the rod receiver for securing at least a portion of the rod in the receiver body.

7. A connector assembly of claim 1, wherein the extension element is monolithically formed with the first end of the connector.

8. A connector assembly for interconnecting a bone fastener and a spinal rod, the connector assembly comprising:
   a connector extending generally along a first rotational axis, having a first end and a second end disposed in co-axial orientation to one another, the first end defining a first cavity around an assembly axis and the second end of the connector adapted to be coupled to a bone fastener;
   a spinal rod receiver having a receiver body coupled to an internally threaded collar in co-axial orientation with the receiver body, the receiver body defining a second cavity around the assembly axis, the second cavity for receiving a spinal rod, the internally threaded collar defining a third cavity, the rod receiver substantially circumscribing the spinal rod and further attachable to the first end of the connector for selectively adjusting the direction of at least a portion of the rod in a coronal plane;
   a washer having an upper face and a lower face, the washer defining a fourth cavity around the assembly axis substantially circumscribing and slidingly coupled to the receiver body, the upper face of the washer being splined or ridged; and a compression member having a hexagonal nut coupled to a retaining flange, the retaining flange having two opposite ends, one end defining a fifth cavity around the assembly axis for receiving the hexagonal nut, the other end of the retaining flange coupled to a threaded shaft, the threaded shaft extending through the fourth cavity of the washer into the threaded collar of the receiver body to secure at least a portion of the rod into the receiver body.

9. A connector assembly of claim 8, wherein the upper splined face of the washer is rotatable 360 degrees in predetermined angular increments in place relative to the first end of the connector to adjust and/or fix the direction of at least a portion of the rod in the coronal plane.

10. A connector assembly of claim 8, wherein the first end of the connector includes a disk having an upper surface and a lower splined surface and defining the first cavity around the assembly axis for receiving the threaded shaft of the rod receiver.

11. A connector assembly of claim 10, wherein the upper splined surface of the washer is configured to mate with the lower splined surface of the disk.

12. A connector assembly of claim 8, wherein the washer further comprises a pair of recesses opposite each other around the circumference of the washer and configured to engage with the spinal rod in the receiver body.

13. A connector assembly of claim 8, wherein the second end of the connector is adapted to extend through a bore defined in a bone fastener.

14. A connector assembly of claim 8, wherein the second end of the connector includes an outer surface having axial splines circumferentially disposed about the outer surface of the second end of the connector.

15. A connector assembly of claim 8, wherein the spinal rod is rotatable to a selected angular orientation for fixation with the first end of the connector.

16. A connector assembly of claim 8, wherein the hexagonal nut comprises a break-off head and the retaining flange is in co-axial orientation with the hexagonal nut and the retaining flange is internally threaded so as to threadingly receive the hexagonal nut at one end and the threaded shaft of the spinal rod receiver at the opposite end.

17. A method for treating a disorder, the method comprising the steps of:

providing an implant assembly comprising:

a bone fastener including a proximal portion and a distal portion, the proximal portion including a bore that defines a first axis, the distal portion defining a longitudinal axis disposed transverse to the first axis, a connector extending generally along a first rotational axis, having a first end and a second end disposed in co-axial orientation to one another, the first end defining a first cavity around an assembly axis and the second end of the connector adapted to be coupled to the bone fastener;

a spinal rod receiver having a receiver body coupled to a threaded shaft defining a second threaded cavity and in co-axial orientation with the receiver body, the receiver body defining a third cavity around the assembly axis, the third cavity for receiving a spinal rod, the rod receiver substantially circumscribing the spinal rod and further attachable to the first end of the connector for selectively adjusting the direction of at least a portion of the rod in a coronal plane;

a washer having an upper face and a lower face, the washer defining a fourth cavity around the assembly axis substantially circumscribing and slidingly coupled to the receiver body, the upper face of the washer being splined or ridged, the upper splined face rotatable 360 degrees in predetermined angular increments in place relative to the first end of the connector to adjust and/or fix the direction of at least a portion of the rod in the coronal plane; and a compression member having a hexagonal nut coupled to a retaining flange having two opposite ends and defining a fifth cavity around the assembly axis, the hexagonal nut co-axial with and engaging with the first end of the connector and the spinal rod receiver, extending through the first cavity of the first end of the connector to engage with the second threaded cavity of the threaded shaft of the rod receiver for securing at least a portion of the rod in the receiver body;

attaching the distal portion of the bone fastener to an iliac bone;

disposing an implant in the receiver body such that the implant is in co-axial relationship with the first end of the connector;

selectively rotating the implant relative to an upper splined face of the first end of the connector to adjust and/or fix the direction of at least a portion of the implant in the coronal plane; and locking the rod receiver with the connector in a selected angular orientation of the implant relative to the connector.

\* \* \* \* \*